United States Patent
Yamane (10) Patent No.: US 12,274,501 B2
(45) Date of Patent: Apr. 15, 2025

(54) OPTICAL SYSTEM, FUNDUS IMAGING APPARATUS, AND FUNDUS IMAGING SYSTEM

(71) Applicant: TAMRON CO., LTD., Saitama (JP)

(72) Inventor: Kodai Yamane, Saitama (JP)

(73) Assignee: TAMRON CO., LTD., Saitama (JP)

( * ) Notice: Subject to any disclaimer, the term of this patent is extended or adjusted under 35 U.S.C. 154(b) by 525 days.

(21) Appl. No.: 17/721,872

(22) Filed: Apr. 15, 2022

(65) Prior Publication Data
US 2022/0409045 A1    Dec. 29, 2022

(30) Foreign Application Priority Data
Jun. 25, 2021    (JP) .................................. 2021-106114

(51) Int. Cl.
*A61B 3/12*    (2006.01)
*A61B 3/00*    (2006.01)
*A61B 3/14*    (2006.01)

(52) U.S. Cl.
CPC .......... *A61B 3/1216* (2013.01); *A61B 3/0008* (2013.01); *A61B 3/14* (2013.01)

(58) Field of Classification Search
CPC ....... A61B 3/1216; A61B 3/0008; A61B 3/14; A61B 3/12
USPC ...................................................... 351/206
See application file for complete search history.

(56) References Cited

U.S. PATENT DOCUMENTS

| | | | | |
|---|---|---|---|---|
| 5,713,047 A | * | 1/1998 | Kohayakawa | A61B 3/12 396/18 |
| 2009/0202113 A1 | * | 8/2009 | Fujii | G06F 21/32 382/117 |
| 2011/0043756 A1 | * | 2/2011 | Kahn | G01N 21/55 351/206 |
| 2016/0213249 A1 | * | 7/2016 | Cornsweet | A61B 3/152 |
| 2019/0290124 A1 | * | 9/2019 | Laforest | A61B 3/12 |

FOREIGN PATENT DOCUMENTS

| | | |
|---|---|---|
| JP | H05-337087 A | 12/1993 |
| JP | H09-028675 A | 2/1997 |
| JP | H09-028677 A | 2/1997 |

OTHER PUBLICATIONS

Miniaturized infrared cameras take colored photos of the eye, Jun. 2018, pp. 1-3, Nara Institute of Science and Technology.

* cited by examiner

*Primary Examiner* — Mohammed A Hasan
(74) *Attorney, Agent, or Firm* — Paratus Law Group, PLLC

(57) ABSTRACT

A fundus imaging apparatus includes an illumination apparatus including a light source and an illumination optical system, and an imaging apparatus including an image sensor and an imaging optical system. The illumination optical system irradiates a fundus with light from the light source. The imaging optical system forms an image of the fundus on the image sensor. An optical axis of the illumination optical system does not match an optical axis of the imaging optical system, or the illumination optical system does not have a specific optical axis.

15 Claims, 6 Drawing Sheets

OPTICAL SYSTEM, FUNDUS IMAGING APPARATUS, AND FUNDUS IMAGING SYSTEM

CROSS-REFERENCE TO RELATED APPLICATIONS

This application is based on and claims the benefit of priority from Japanese Patent Application No. 2021-106114, filed on Jun. 25, 2021, the entire contents of which are incorporated herein by reference.

BACKGROUND OF THE INVENTION

Technical Field

The present invention relates to an optical system, a fundus imaging apparatus, and a fundus imaging system.

Related Art

Three major causes of blindness in Japanese are known: diabetic retinopathy, age-related macular degeneration, and glaucoma. Fundus examination is effective for early detection of these diseases. In a fundus camera used in fundus examination, an optical system of coaxial vertical illumination in which an optical axis of light incident on an eye matches an optical axis of reflected light reflected by the fundus is used.

For such an optical system, a method of preventing overlapping of optical paths of irradiation light and reflected light by separating the irradiation light (for example, refer to JP 9-28677 A and JP 5-337087 A), a method of imaging unnecessary light and shielding the unnecessary light (for example, refer to JP 9-28675 A), and a method of shielding unnecessary light using a linear polarization element (for example, refer to Nara Institute of Science and Technology, Science and Technology Agency, "Development of a compact fundus camera system for selfie without shaking and glaring", [online], Jun. 18, 2018, jointly announced by JST, [retrieved on Jan. 14, 2020], Internet (URL: https://www.jst-.go.jp/pr/announce/20180618/index.html)) are known.

SUMMARY OF THE INVENTION

However, in the technique in the related art, an optical system of coaxial vertical illumination in which an optical axis of light incident on an eye matches an optical axis of reflected light reflected by the fundus is used. The technique in the related art has a problem that unnecessary light reflected by a portion of the eye other than the fundus is mixed with light for forming a fundus image and artifacts such as a ghost flare may occur.

For example, in the methods described in JP 9-28677 A and JP 5-337087 A, in a case where the irradiation light has a wide angle, most of the optical paths of the irradiation light and the reflected light overlap with each other, and as a result, an occurrence of a ghost flare cannot be prevented. In the method described in JP 9-28675 A, in a case where the irradiation light has a wide angle, an image of unnecessary light becomes large, and as a result, necessary light is also blocked. In the method described in "Development of a compact fundus camera system for selfie without shaking and glaring", in a case where the irradiation light has a wide angle, a four-leaf ghost may remain due to rotation of polarized light by reflection. For this reason, in a technical field of fundus observation, a technique capable of preventing occurrence of artifacts is required.

An object of an aspect of the present invention is to provide a technique capable of preventing occurrence of artifacts in imaging of the fundus.

In order to solve the above problem, according to an aspect of the present invention, there is provided an optical system including: an illumination optical system configured to irradiate a fundus of an eyeball of a subject with light from a light source; and an imaging optical system configured to form an image of the fundus on an image sensor, in which an optical axis of the illumination optical system does not match an optical axis of the imaging optical system, or the illumination optical system does not have a specific optical axis.

In addition, in order to solve the above problem, according to another aspect of the present invention, there is provided a fundus imaging apparatus including: an illumination apparatus including a light source and the illumination optical system; and an imaging apparatus including an image sensor and the imaging optical system.

Further, in order to solve the above problem, according to still another aspect of the present invention, there is provided a fundus imaging system including the fundus imaging apparatus.

According to an aspect of the present invention, it is possible to provide a technique capable of preventing occurrence of artifacts in imaging of the fundus.

DESCRIPTION OF THE EMBODIMENTS

[Outline]

Figure 1:
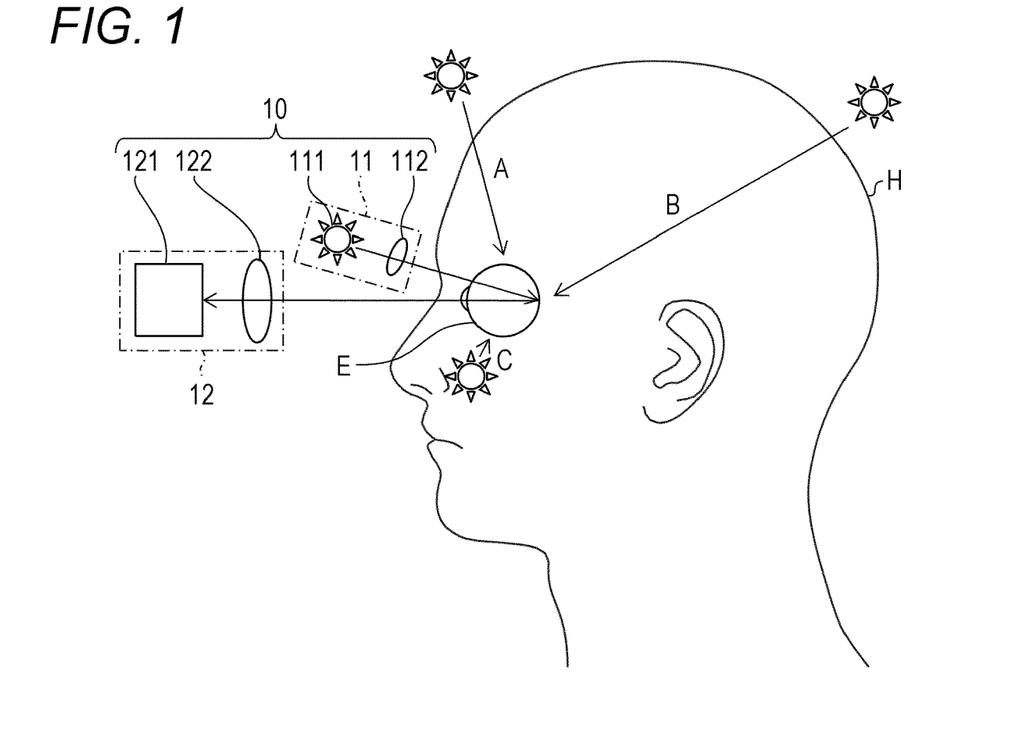
FIG. 1 is a diagram schematically illustrating an example of a configuration and a use form of a fundus imaging apparatus according to an embodiment of the present invention.

FIG. 1 is a diagram schematically illustrating a schematic configuration and a usage form of a fundus imaging system according to an embodiment of the present invention. The fundus imaging system according to the embodiment of the present invention includes a fundus imaging apparatus 10. The fundus imaging apparatus 10 includes an illumination apparatus 11 and an imaging apparatus 12.

[Illumination Apparatus]

The illumination apparatus 11 includes a light source 111 and an illumination optical system 112. The light source 111 may be any light source that can be used for fundus observation, may be a light source that intermittently emits light such as a strobe, or may be a light source that continuously emits light. More preferably, the light source 111 is a light source that continuously emits light. Examples of the light source that continuously emits light include a light bulb, a laser diode (LD), and a light emitting diode (LED). Preferably, a wavelength of the light from the light source 111 is equal to or higher than 600 nm from a viewpoint of preventing a miosis reaction due to irradiation with the light from the light source 111. Further, preferably, the wavelength of the light from the light source 111 is equal to or lower than 1600 nm from a viewpoint of preventing attenuation of irradiation light due to absorption of the light into water in a living body.

The wavelength of the light from the light source 111 is preferably 650 nm to 1000 nm, which is also referred to as a so-called living body window, and more preferably 800 nm to 900 nm from a viewpoint of preventing attenuation of the light in a living body. In this specification, "to" means a range of "equal to or higher than and equal to or lower than" including numerical values at both ends.

The illumination optical system 112 is an optical system that irradiates a fundus of an eyeball E of a subject H with light. The illumination optical system 112 focuses, refracts, and reflects the light from the light source 111 as necessary. The illumination optical system 112 may be configured with known optical elements such as a lens, a prism, a beam splitter, a polarizer, a reflection member, a light flux control member, a solid-state semiconductor element, and a thermal light source. Examples of the solid-state semiconductor element include a light emitting diode (LED), a semiconductor laser (LD), a laser (LASER), and an electroluminescent (EL) element. These optical elements are supported in a desired positional relationship with respect to the light source 111 or between a plurality of optical elements by an appropriate member such as a tube or a casing. The optical elements may be movably supported along an optical axis.

[Imaging Apparatus]

The imaging apparatus 12 includes an image sensor 121 and an imaging optical system 122. The image sensor 121 may be a known solid state image sensor that can be used for fundus imaging. Examples of the image sensor include a CCD image sensor and a CMOS image sensor. These image sensors may be color sensors or monochrome sensors. More preferably, the image sensor is a monochrome sensor from a viewpoint of higher image quality.

The imaging optical system 122 is an optical system that forms an image of the fundus on the image sensor 121. The imaging optical system 122 forms an image by focusing the light from the fundus, and forms the image on the image sensor 121 by refracting or reflecting the light as necessary. Similarly to the illumination optical system 112, the imaging optical system 122 may be configured with known optical elements, and the optical elements are supported in a desired positional relationship with respect to the light source 111 or between a plurality of optical elements by an appropriate member such as a tube or a casing. The optical elements of the imaging optical system 122 may also be movably supported along the optical axis.

[Description of Optical System]

In the embodiment of the present invention, the optical axis of the illumination optical system 112 that irradiates the fundus with the light from the light source 111 does not match the optical axis of the imaging optical system 122. In the embodiment of the present invention, "the optical axis of the illumination optical system does not match the optical axis of the imaging optical system" means that a part or a whole of the optical axis of the illumination optical system does not substantially match the optical axis of the imaging optical system. For example, in the above-described coaxial vertical illumination, usually, a part of the optical axis of the illumination optical system substantially matches the optical axis of the imaging optical system from the outside of the front of the eyeball to the fundus, and as a result, the optical axes are displayed to be overlapped in an image. In the embodiment of the present invention, the optical axis of the illumination optical system 112 does not include a portion matching (overlapping) with the optical axis of the imaging optical system 122.

Alternatively, in the embodiment of the present invention, the illumination optical system 112 does not have a specific optical axis. "The illumination optical system does not have a specific optical axis" means that the illumination optical system is an asymmetric system or a non-imaging system and is an illumination system in which no optical axis exists. Examples of the illumination system include an LED that is directly provided for irradiation of an eyeball with light and an optical system with diffusion of light of a light source such as a headlight of a vehicle. The illumination system may also be the illumination optical system in the embodiment of the present invention.

In the embodiment of the present invention, the light from the fundus is typically extracted via a pupil. Thus, the imaging optical system 122 is located in front of the eyeball E. The illumination optical system 112 is usually disposed at a position serving as an optical axis along a direction intersecting with the optical axis of the imaging optical system 122. From the position, the illumination apparatus 11 irradiates the fundus with the light from the light source 111 via the illumination optical system 112.

[Description of Eye as Irradiation Target]

In the embodiment of the present invention, the fundus means a portion inside a crystalline lens of the eyeball E. The fundus may be the entirety or a part of the portion of the eyeball E. For example, the fundus may be a retina. Here, a form in which the retina is imaged as the fundus will be described as an example.

Figure 2:
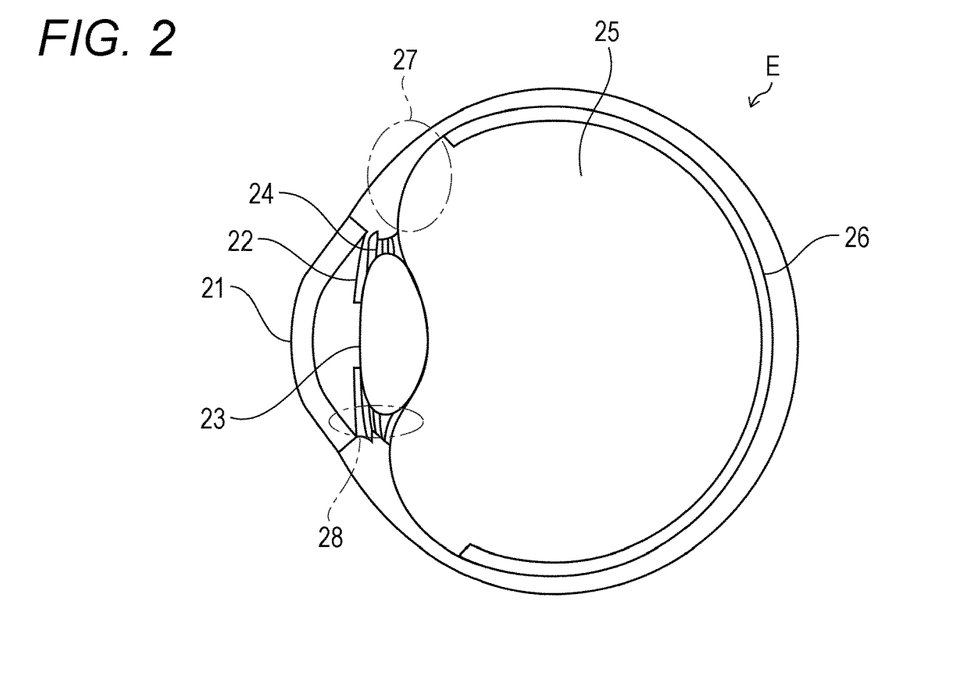
FIG. 2 is a diagram schematically illustrating a portion in an eyeball that is suitable for irradiation with light from a light source in the embodiment of the present invention.

FIG. 2 is a diagram schematically illustrating a portion in the eyeball E that is suitable for irradiation with the light from the light source 111 in the embodiment of the present invention. As illustrated in FIG. 2, the eyeball E includes a cornea 21, an iris 22, a crystalline lens 23, a zonule-of-Zinn 24, a vitreous body 25, and a retina 26 from the front. The vitreous body 25 and the retina 26 correspond to the above-described fundus.

Further, the eyeball E includes a trans-pars-plana region 27 and an iris-and-zonule-of-Zinn region 28. The trans-pars-plana region 27 is a region from an end portion of the retina 26 to the zonule-of-Zinn 24. The trans-pars-plana region 27 is a region in which the retina 26 is not interposed between the vitreous body 25 and a surface of the eyeball E. The iris-and-zonule-of-Zinn region 28 is a region in which the iris 22 and the zonule-of-Zinn 24 overlap with each other. The iris-and-zonule-of-Zinn region 28 is a region in which the crystalline lens 23 is not interposed between the iris 22 and the vitreous body 25. Although not illustrated, a fat tissue called orbital fat exists around the eyeball E.

[Description of Light Irradiation]

The illumination optical system 112 may be an optical system that directly irradiates the fundus of the eyeball E of the subject H with light. Here, "direct irradiating" means irradiating the fundus with light by making the light from the light source 111 direct toward the fundus to be imaged and transmit through an anterior segment tissue on an optical path. In this case, preferably, the illumination optical system 112 is configured to directly irradiate the fundus with the light from the light source 111 without making the light pass through the crystalline lens. The illumination optical system 112 directly irradiates the fundus with the light, and thus an image of the fundus by reflected light is obtained. Preferably, the illumination optical system 112 is an optical system that directly irradiates the fundus with light from a viewpoint of preventing occurrence of artifacts or from a viewpoint of more brightly illuminating the fundus. Further, preferably, the illumination optical system 112 is an optical system that directly irradiates the fundus with light without making the light pass through the crystalline lens from a viewpoint of preventing the subject H from feeling glare.

Preferably, the illumination optical system 112 is an optical system that irradiates the fundus with the light from the light source 111 via the trans-pars-plana region 27 of the eyeball E. In a case of illuminating the fundus via the trans-pars-plana region 27, the light from the illumination optical system 112 reaches the vitreous body 25 or the retina 26 without passing through the retina 26. Thus, preferably, the illumination optical system 112 irradiates the fundus with the light via the trans-pars-plana region 27 from a viewpoint of preventing the subject H from feeling glare and from a viewpoint of more brightly illuminating the fundus.

Further, preferably, the illumination optical system 112 is an optical system that irradiates the fundus with the light from the light source 111 via the iris-and-zonule-of-Zinn region 28 of the eyeball E. In a case of illuminating the fundus via the iris-and-zonule-of-Zinn region 28, the light from the illumination optical system 112 reaches the vitreous body 25 or the retina 26 without passing through the crystalline lens 23. Thus, preferably, the illumination optical system 112 irradiates the fundus with the light via the iris-and-zonule-of-Zinn region 28 from a viewpoint of preventing the subject H from feeling glare and from a viewpoint of more brightly illuminating the fundus.

The illumination optical system 112 may be an optical system that indirectly irradiates the fundus of the eyeball E of the subject H with light. Here, "indirect irradiating" means irradiating a surrounding tissue of the eyeball E with the light from the light source 111 and illuminating the fundus with scattered light by the orbital fat. Examples of the surrounding tissue include an orbital fat, a sclera, a muscle tissue, and a neural tissue. In the following description, an orbital fat is described as an example of the surrounding tissue. In this case, the illumination optical system 112 may be, for example, an optical system that irradiates the orbital fat around the eyeball E with the light from the light source 111 via a biological tissue of the subject H. The illumination optical system 112 irradiates the orbital fat with the light. Thereby, the eyeball E is illuminated from behind the crystalline lens by scattered light by the orbital fat, and thus an image of the light transmitting through the fundus from behind the eyeball is obtained. Preferably, the illumination optical system 112 illuminates the fundus via the orbital fat from a viewpoint of more reliably preventing the subject H from feeling glare and preventing an occurrence of an artifact.

More specifically, the illumination optical system 112 that indirectly irradiates the fundus of the eyeball E of the subject H with light may be an optical system that irradiates a fat tissue around the eyeball E with the light from the light source via a skull of the subject H. In this case, the illumination optical system may be disposed so as to irradiate a frontal region or a top region of a head of the subject H with the light from the light source as indicated by an arrow A in FIG. 1, or may be disposed so as to irradiate a temporal region or an occipital region of the subject H with the light from the light source as indicated by an arrow B in FIG. 1. In the above case, preferably, the illumination optical system is an optical system that irradiates a fat tissue around the eyeball E with the light from the light source via a plurality of portions of a skull of the subject H from a viewpoint of more brightly illuminating the fundus.

Alternatively, the illumination optical system that indirectly irradiates the fundus of the eyeball E of the subject H with light may be an optical system that irradiates a fat tissue around the eyeball E with the light from the light source via an ethmoid bone of the subject H as indicated by an arrow C in FIG. 1. The illumination optical system irradiates the ethmoidal bone of the subject H with the light from the light source. Thereby, the fundus is irradiated with the light, from a nasal cavity via an ethmoidal sinus and an orbital fat. The illumination apparatus may be configured with an optical system including an optical element such as an optical fiber that can be inserted into a nasal cavity of the subject H, or an optical system including a small light source and an optical element such as a light flux control member that directs light of the light source toward an ethmoidal bone of the subject H. Preferably, the illumination optical system illuminates the fundus via the ethmoidal bone from a viewpoint of brightly illuminating the fundus from below or behind the eyeball and from a viewpoint of easily stabilizing conditions for illuminating the eyeball such as a condition of a position of the light source.

In a case where the illumination optical system 112 irradiates the fundus of the subject H with the light, preferably, an area of a portion to be irradiated in the subject H is set to be larger from a viewpoint of more brightly illuminating the fundus. In this case, the illumination optical system 112 may be an optical system that irradiates specific small regions around the eye of the subject H with the light from the light source 111. On the other hand, preferably, the illumination optical system 112 is an optical system that irradiates a specific region having a sufficient area with the light from a viewpoint of more brightly illuminating the fundus.

Figure 3:
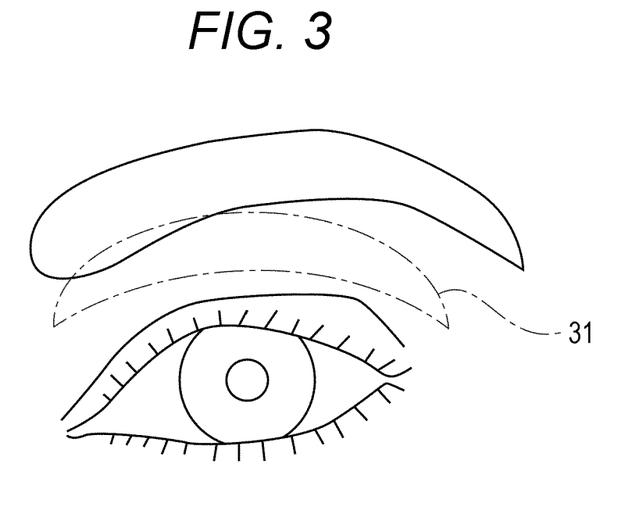
FIG. 3 is a diagram schematically illustrating an example of a portion on a face of a subject that is suitable for irradiation with the light from the light source in the embodiment of the present invention.

FIG. 3 is a diagram schematically illustrating an example of a portion on a face of the subject H that is suitable for irradiation with the light from the light source 111 in the embodiment of the present invention. As illustrated in FIG. 3, the illumination optical system 112 may be an optical system that illuminates an arc region 31 including an upper eyelid of the subject H with the light from the light source 111.

Figure 4:
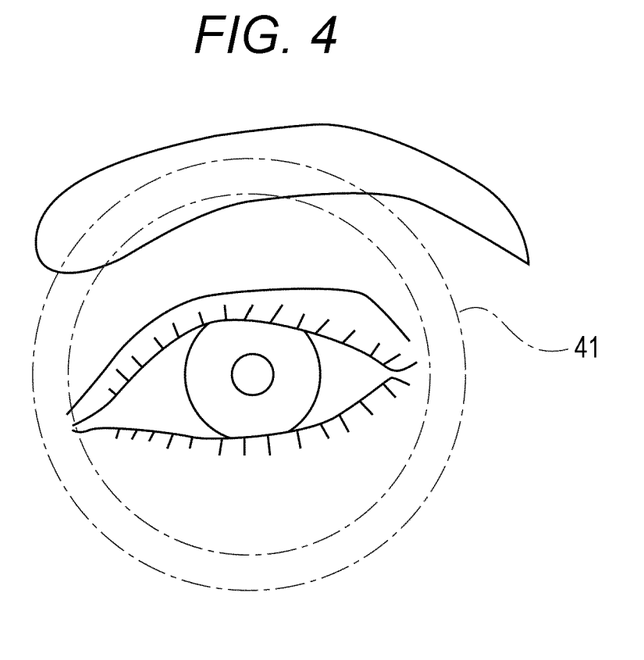
FIG. 4 is a diagram schematically illustrating another example of a portion on the face of the subject that is suitable for irradiation with the light from the light source in the embodiment of the present invention.

FIG. 4 is a diagram schematically illustrating another example of a portion on a face of the subject H that is suitable for irradiation with the light from the light source 111 in the embodiment of the present invention. As illustrated in FIG. 4, the illumination optical system 112 may be an optical system that illuminates an annular region 41 including an upper eyelid and a lower eyelid of the subject H with the light from the light source 111.

As described above, the illumination optical system 112 may be an optical system that irradiates the fundus with the light from the light source 111 via the arc region 31 or the annular region 41 around the eye on the face of the subject H. The optical system may be configured using a reflection member, a light flux control member, a light shielding member that shields light in a specific direction, or the like.

In a case where the illumination optical system 112 irradiates a specific region on the face of the subject H with the light from the light source 111 as described above, preferably, an area of the region to be irradiated with the light is set to be larger from a viewpoint of more brightly illuminating the fundus. From the viewpoint, an area of the region to be irradiated with the light is preferably equal to or larger than 1 $cm^2$, and more preferably equal to or larger than 2 $cm^2$. Assuming that a skull is a sphere having a radius of 15 cm, an area of the region may be equal to or smaller than 700 $cm^2$ from a viewpoint of sufficiently brightly illuminating the fundus.

Hereinafter, embodiments of the present invention will be more specifically described.

First Embodiment

[Fundus Imaging System]

Figure 5:
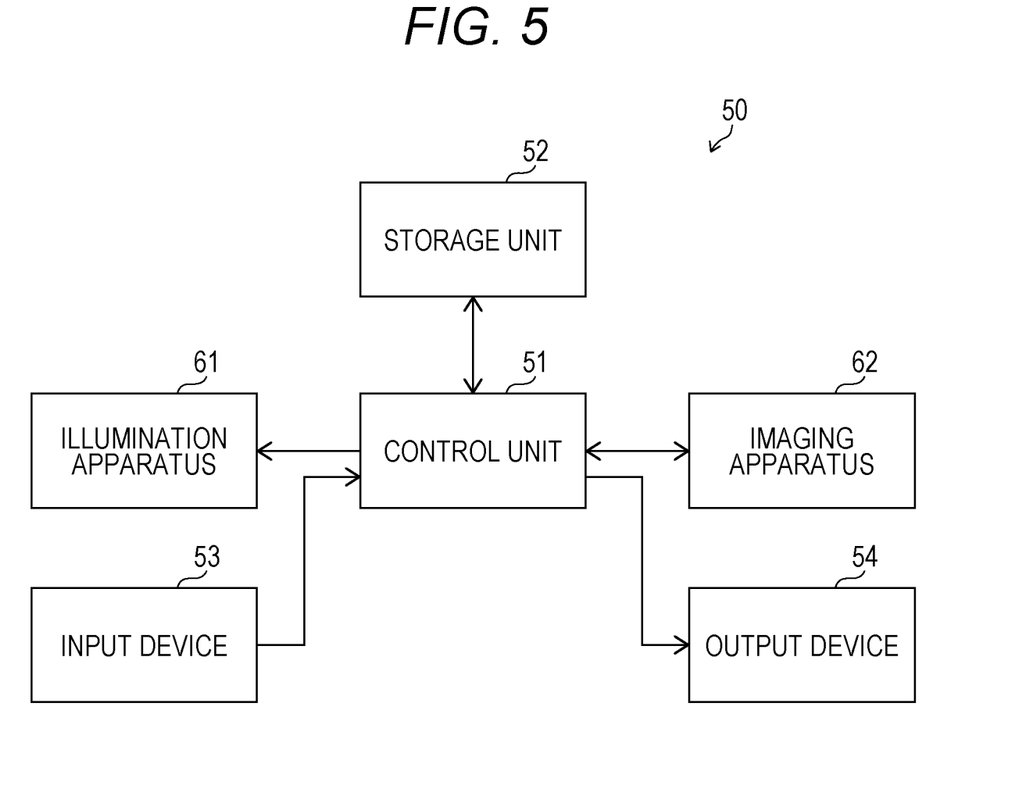
FIG. 5 is a block diagram illustrating an example of a functional configuration of a fundus imaging system according to a first embodiment of the present invention.

FIG. 5 is a block diagram illustrating an example of a functional configuration of a fundus imaging system according to a first embodiment of the present invention. As illustrated in FIG. 5, a fundus imaging system 50 includes an illumination apparatus 61, an imaging apparatus 62, and a control unit 51. The fundus imaging system 50 further includes a storage unit 52, an input device 53, and an output device 54.

The illumination apparatus 61 and the imaging apparatus 62 respectively have configurations similar to the configurations of the above-described illumination apparatus 11 and the above-described imaging apparatus 12. The configurations of the illumination apparatus 61 and the imaging apparatus 62 will be described in more detail later.

The control unit 51 controls operations of various devices related to imaging of the fundus according to input signals from the various devices as necessary. The storage unit 52 stores information for controlling the imaging of the fundus by the control unit 51, and stores information on the imaging of the fundus as necessary. The storage unit 52 is configured with, for example, a nonvolatile recording medium such as an HDD, an SSD, or a DVD-RAM.

The input device 53 is a device that allows the subject H or an operator of the fundus imaging system to input information on the imaging of the fundus to the control unit 51. The input device 53 is, for example, a keyboard, a touch panel, an audio input device, or a reception device.

The output device 54 is a device that outputs image data of the fundus or information on the imaging of the fundus from the control unit. The output device 54 is, for example, a display, an audio output device, or a transmission device.

[Fundus Imaging Apparatus]

<Configuration of Apparatus>

Figure 6:
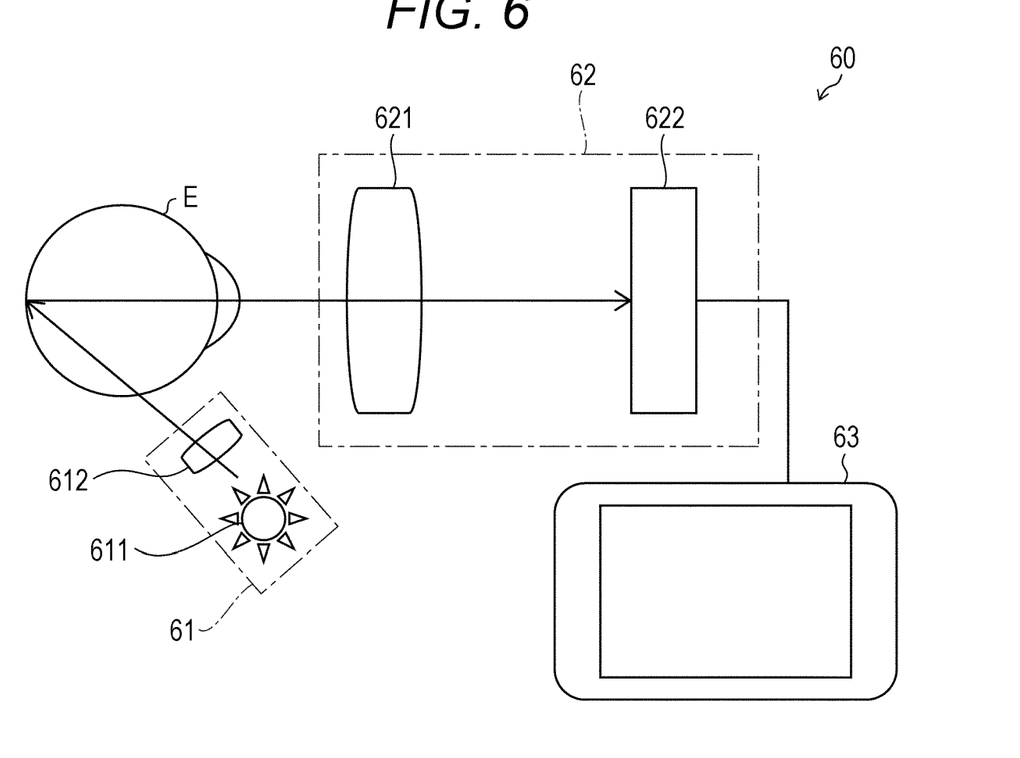
FIG. 6 is a diagram schematically illustrating a configuration of a fundus imaging apparatus according to the first embodiment of the present invention.

FIG. 6 is a diagram schematically illustrating a configuration of a fundus imaging apparatus 60 according to the first embodiment of the present invention. As illustrated in FIG. 6, the fundus imaging apparatus 60 includes the illumination apparatus 61, the imaging apparatus 62, and a monitor 63. In the fundus imaging apparatus 60, an optical axis of emitted light in the illumination apparatus 61 and an optical axis of received light in the imaging apparatus 62 are independent from each other, and do not have a common portion. As described above, the fundus imaging apparatus 60 has a structure that does not include an optical system of coaxial vertical illumination.

The illumination apparatus 61 includes a light emitting diode (LED) 611 and a lens 612. The LED 611 and the lens 612 are integrally held in an appropriate positional relationship by, for example, a tube or a casing. The LED 611 outputs light having a wavelength of 600 nm to 1600 nm. The LED 611 corresponds to the above-described light source. The lens 612 receives the light from the LED 611, and focuses the light on the fundus (retina) of the eyeball E from a direction oblique to the front of the eyeball E of the subject H. The lens 612 corresponds to the above-described illumination optical system. The illumination apparatus 61 does not include an eyepiece portion that is brought into contact with a portion around the eye of the subject H, and is disposed away from the subject H. Further, the illumination apparatus 61 is not relatively fixed to the imaging apparatus 62, and a position of the illumination apparatus 61 can be adjusted around the eyeball E of the subject H.

The imaging apparatus 62 includes a lens 621 and a CMOS image sensor 622. The lens 621 and the CMOS image sensor 622 are integrally held in an appropriate positional relationship by, for example, an eyepiece casing or a tube. The lens 621 receives, from the front of the eyeball E, the light from the fundus (retina), and focuses the light on the CMOS image sensor 622. The lens 621 corresponds to the above-described imaging optical system. The CMOS image sensor 622 corresponds to the above-described image sensor.

The monitor 63 is a liquid crystal display device, and displays information on the imaging of the fundus such as information which is input from the input device 53 or image data which is obtained by imaging the fundus. The monitor 63 corresponds to the above-described output device 54.

[Description of Imaging of Fundus]

An example of a flow of processing for the imaging of the fundus by the fundus imaging system according to the present embodiment will be described. The control unit 51 operates the illumination apparatus 61 and the imaging apparatus 62 according to information for giving an instruction on a start of fundus imaging from the input device 53. Alternatively, the control unit 51 operates the illumination apparatus 61 in a case where the eyeball E of the subject H is at a specific position in the image data from the imaging apparatus 62.

The illumination apparatus 61 causes the LED 611 to output light according to a signal for giving an instruction on an operation from the control unit 51. Further, the illumination apparatus 61 adjusts a distance between the LED 611 and the lens 612 in an optical axis direction according to the signal as necessary, and adjusts focusing of the light on the face or the fundus of the subject H. The lens 612 receives the light from the LED 611, and directly irradiates the fundus of the eyeball E of the subject H with the light. The light with which the fundus is irradiated is reflected by the fundus.

Alternatively, the lens 612 receives the light from the LED 611, and irradiates an orbital fat around the eyeball E of the subject H with the light. The scattered light by the orbital fat transmits through the fundus from behind the eyeball.

The imaging apparatus 62 adjusts focusing of the light from the eyeball E of the subject H and imaging in the CMOS image sensor 622 according to a signal for giving an instruction on an operation from the control unit 51. At that time, the imaging apparatus 62 adjusts the distance between the CMOS image sensor 622 and the lens 621 in the optical axis direction according to the signal as necessary. The lens 621 forms an image of the fundus by receiving the light (reflected light or transmitted light) from the fundus, and focuses the light on the CMOS image sensor 622. The CMOS image sensor 622 detects the light from the lens 621, and transmits a signal according to the detected light to the control unit 51. The control unit 51 outputs information of the image of the fundus to the monitor 63, and causes the monitor 63 to display the image of the fundus according to the signal from the imaging apparatus 62.

Figure 7:
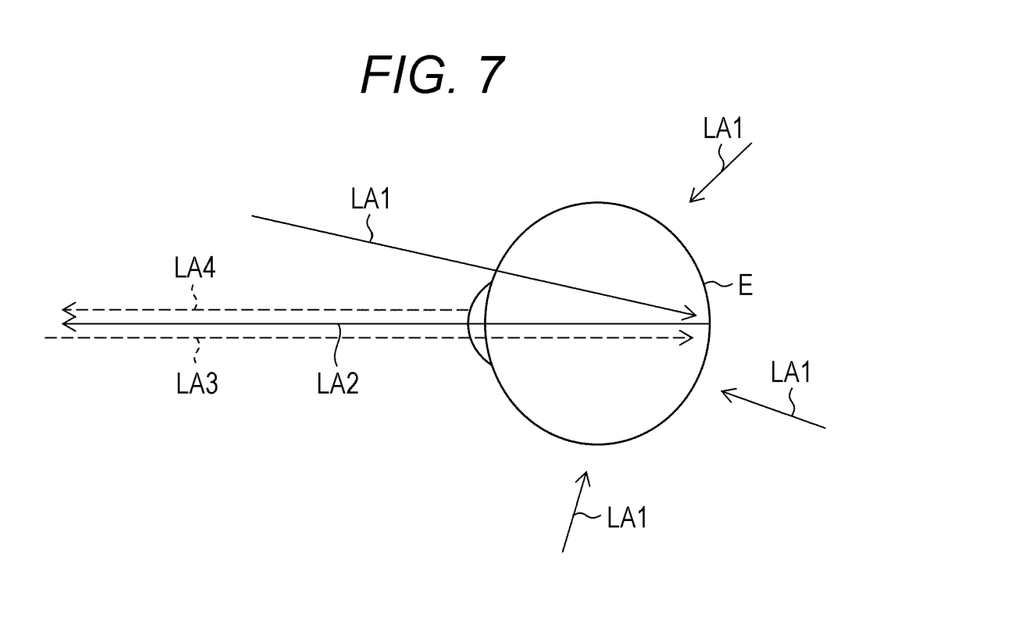
FIG. 7 is a diagram for explaining a difference between the embodiment of the present invention and a form in the related art.

In the present embodiment, a fundus image which is not substantially influenced by the reflected light on the surface of the eyeball E and has a high image quality is formed. FIG. 7 is a diagram for explaining a difference between the embodiment of the present invention and a form in the related art. In FIG. 7, a solid-line arrow represents an optical axis of light in the embodiment of the present invention. In FIG. 7, a broken-line arrow represents an optical axis of light in the form in the related art.

In the embodiment of the present invention, as described above, an optical system of coaxial vertical illumination is not included. Thus, as illustrated in FIG. 7, the fundus is irradiated with the light from the LED 611 such that the optical axis LA1 of the light of the lens 621 extends in a direction other than the front of the eyeball E, for example, in a direction oblique to the front of the eyeball E. The reflected light by the fundus is extracted to the front of the eyeball E via a pupil. That is, the optical axis LA2 of the light from the fundus extends in a direction of the front of the eyeball E. As described above, in the present embodiment, the optical axis of the illumination optical system that irradiates the fundus with the light from the light source does not match the optical axis of the imaging optical system. Therefore, in the CMOS image sensor 622, the reflected light on the surface of the eyeball E is not substantially detected, and a fundus image which does not substantially include an image of the reflected light and has a high image quality is formed.

On the other hand, in a case where an optical system of coaxial vertical illumination is included as in the related art, the fundus is irradiated with the light from the light source from the front of the eyeball E, and the reflected light by the fundus is extracted from the front of the eyeball E. Therefore, both the optical axis LA3 of the light from the light source in the related art and the optical axis LA2 of the light from the fundus extend in a direction of the front of the eyeball E, and substantially match each other. Further, a part of the light from the light source is reflected by a surface of the cornea. The optical axis LA4 of the reflected light on the surface also extends in the direction of the front of the eyeball E, and substantially matches the optical axis LA2 and the optical axis LA3. For this reason, in the related art, since the image sensor detects the reflected light on the surface of the eyeball E together with the light from the eyeball E, artifacts caused by the reflected light on the surface of the eyeball E are included in a fundus image. In a case where the reflected light on the surface of the eyeball E that is directed to the image sensor is blocked, in formation of a fundus image, a fundus image including a portion overlapping with the artifacts is not formed, and a fundus image in which a portion corresponding to the artifacts is missed is formed.

In the related art, in a time-division type fundus imaging apparatus using a light source that intermittently emits light, such as a flash or a scanning laser ophthalmoscope (SLO), illumination is set to be within a range of safety standards. Further, in the fundus, reflectance of light on the retina is not high. For this reason, many photon statistics cannot be acquired in imaging of the retina, and as a result, it is disadvantageous to perform spectroscopic observation of the fundus (retina). In the present embodiment, sufficiently many photon statistics can be easily acquired.

In addition, in the present embodiment, it is possible to illuminate the fundus with constant irradiation light from the illumination optical system. Thus, the present embodiment is advantageous as compared with the SLO from a viewpoint of uniformly illuminating the fundus. Therefore, in the present embodiment, as compared with the SLO, the fundus can be imaged under more stable imaging conditions, and imaging data having a higher image quality can be acquired.

As described above, in the fundus imaging apparatus in the related art, it is difficult to image the fundus due to an influence of an artifact. This tendency is more remarkable as the angle is wider. For this reason, the image quality of the image of the fundus is deteriorated due to the image of the artifacts included in the image of the fundus, and as a result, it may be more difficult to perform a diagnosis based on the image of the fundus.

In the embodiment of the present invention, the image of the artifacts is substantially not included in the image of the fundus. Therefore, the above-described problem does not occur, and a high-quality image of the fundus can be imaged even in a case of, for example, the subject H having a small pupil diameter. In addition, a transmission image of the fundus can be imaged by performing backlight irradiation of illuminating a portion around the eyeball E from a portion having an area other than the pupil of the subject H by the above-described indirect irradiation. Thereby, a high-accuracy image of the fundus can be easily acquired.

Further, in the present embodiment, the imaging optical system includes the lens 621 that realizes light focusing and imaging. Therefore, the configuration of the imaging optical system in the fundus imaging apparatus is simplified as compared with a case where the imaging optical system includes a primary imaging optical system that forms an image of the fundus by receiving the light from the fundus and a secondary imaging optical system that reforms the image on the image sensor. Thereby, in the present embodiment, the entire fundus imaging apparatus can be more compactly configured.

Second Embodiment

Figure 8:
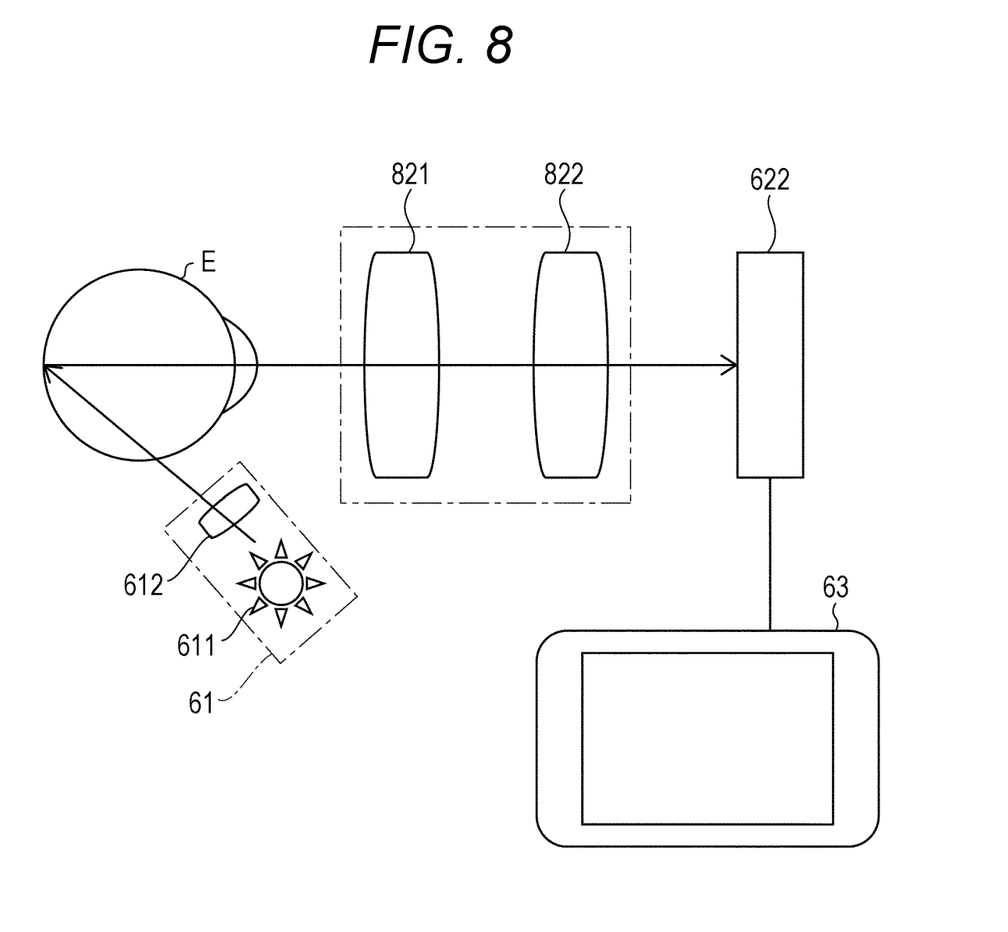
FIG. 8 is a diagram schematically illustrating a configuration of a fundus imaging apparatus according to a second embodiment of the present invention.

Another embodiment of the present invention will be described below. For convenience of description, members having the same functions as the members described in the above-described embodiment are denoted by the same reference numerals, and a description thereof will not be repeated. FIG. 8 is a diagram schematically illustrating a configuration of a fundus imaging apparatus according to a second embodiment of the present invention. The configuration of the fundus imaging apparatus according to the present embodiment is the same as the configuration according to the above-described first embodiment, except for the configuration of the imaging optical system.

As illustrated in FIG. 8, the imaging optical system according to the present embodiment includes two lenses 821 and 822. These lenses 821 and 822 are supported in a casing or a tube with which the eye of the subject H can be brought into contact. The lens 821 forms an image of the fundus by receiving the light from the fundus. The lens 822 reforms the image of the fundus that is formed by the lens 821 on the CMOS image sensor 622. As described above, in the present embodiment, the imaging optical system includes both the optical element of the primary imaging optical system and the optical element of the secondary imaging optical system.

As described above, in the present embodiment, the imaging optical system is an optical system including a typical secondary imaging optical system. The present embodiment is more advantageous as compared with the above-described first embodiment from a viewpoint of forming a high-quality image of the fundus even in a case of a wide angle.

Third Embodiment

Figure 9:
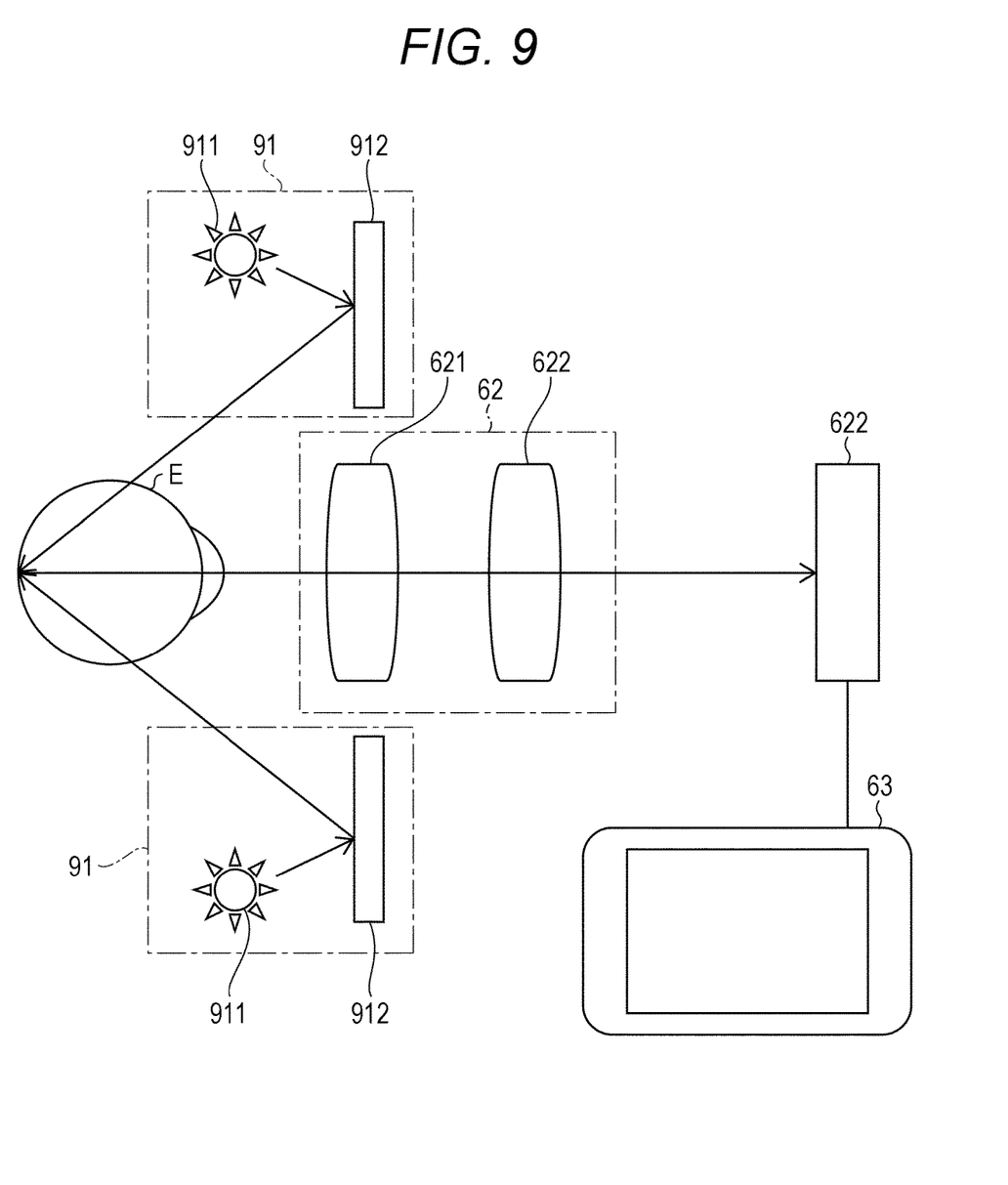
FIG. 9 is a diagram schematically illustrating a configuration of a fundus imaging apparatus according to a third embodiment of the present invention.

Another embodiment of the present invention will be described below. For convenience of description, members having the same functions as the members described in the above-described embodiment are denoted by the same reference numerals, and a description thereof will not be repeated. FIG. 9 is a diagram schematically illustrating a configuration of a fundus imaging apparatus according to a third embodiment of the present invention. The configuration of the fundus imaging apparatus according to the present embodiment is the same as the configuration according to the above-described second embodiment, except for the configuration of the illumination apparatus.

As illustrated in FIG. 9, an illumination apparatus 91 according to the present embodiment includes a light source 911 and a reflection member 912. A plurality of light sources 911 are disposed around and in the vicinity of the eyeball E of the subject H. For example, a plurality of light sources 911 are disposed in the vicinity of the eyelid of the subject H and around the lens 621 of the imaging optical system. The light sources 911 may be disposed at equal intervals in an annular shape, or may be disposed at appropriate intervals in an asymmetric shape according to a shape of a human body.

The reflection member 912 is a member for reflecting the light from the light source 911 toward the portion around the eyeball E (for example, the eyelid, the trans-pars-planar region, and the like), and is, for example, a reflection mirror that totally reflects the light from the light source 911. The reflection mirror is disposed, for example, at a position farther from the eyeball E than the light source 911 and in the vicinity of or around the lens 621 of the imaging optical system. The illumination apparatus 91 according to the present embodiment irradiates a region around the pupil that has a certain shape and has an area with the light from the light source 911. The area of the region is preferably equal to or larger than 1 cm$^2$, and more preferably equal to or larger than 2 cm$^2$ from a viewpoint of forming a sufficiently clear image of the fundus. In addition, it is desirable that the region includes a circumferential portion of the cornea (for example, the iris-and-zonule-of-Zinn region) of the eyeball E to be examined.

The present embodiment is more advantageous as compared with the above-described embodiment of the present invention from a viewpoint of more uniformly illuminating the portion in the vicinity of and around the eyeball E of the subject H. Further, in the present embodiment, the region irradiated with the light from the light source 911 is wide, and thus luminance of the light can be further reduced. Therefore, the present embodiment is more advantageous as compared with the above-described embodiment of the present invention from a viewpoint of further reducing a load on the subject H and the eyeball E or preventing an occurrence of the load even in a case where the light from the light source reaches the fundus via the pupil.

In the present embodiment, the illumination optical system may be configured using an optical element that illuminates a desired position around the eyeball E by refracting the light from the light source 911, instead of the reflection member. Alternatively, in the present embodiment, the illumination optical system may be configured by combining an optical element and a reflection member that refract the light from the light source 911. Examples of the optical element that refracts the light from the light source 911 include a prism and a light flux control member. According to this configuration, effects of the present embodiment described above can also be achieved.

Other Embodiments

The fundus imaging system, the fundus imaging apparatus, and the optical system according to the embodiment of the present invention may include configurations other than the above-described configurations within a range in which the effects of the embodiment of the present invention can be obtained.

For example, the illumination apparatus may be disposed in contact with the subject. The illumination apparatus may include only a light source that emits light in a state of being in contact with the subject. Alternatively, the illumination apparatus may be configured such that an object-side end surface of the illumination optical system comes into contact with the subject when in use. Alternatively, the illumination apparatus may be configured such that a position of the head of the subject with respect to the illumination optical system when in use is determined by a frame body which supports the illumination optical system. This configuration is advantageous from a viewpoint of enhancing stability of conditions of the fundus imaging and from a viewpoint of simplifying the configuration of the fundus imaging apparatus.

Further, the imaging apparatus may not include an eyepiece portion, and may be disposed away from the subject H. This configuration is preferable from a viewpoint of realizing non-contact fundus imaging with respect to the subject H. By realizing non-contact fundus imaging, an examination can be more simply performed.

Further, in the embodiment of the present invention, the illumination apparatus may be one type or more, and the fundus imaging apparatus may be configured to perform one or both of direct irradiation and indirect irradiation at a time.

Further, in the embodiment of the present invention, the fundus imaging system may further include an addition processing unit that performs processing of composing an image by adding a signal corresponding to light detected by the image sensor, in addition to control for imaging the fundus. According to this configuration, many photon statistics can be acquired. Therefore, this configuration is advantageous from a viewpoint of forming a clear image of the fundus even in a case where the fundus is illuminated with a small amount of light.

Further, in the embodiment of the present invention, the fundus imaging system may further include an internal imaging processing unit that performs processing of imaging an internal structure of the subject H from a signal corresponding to light detected by the image sensor. The processing may be performed by a technique of realizing diffuse optical tomography (DOT). The diffuse optical tomography is a technique of detecting diffuse light in a living body and imaging an optical characteristic value in a living tissue. As a result, information on a structure and metabolism in a specific region of a living body can be quantitatively detected. In a case where the fundus imaging system further includes the above-described internal imaging processing unit, preferably, the fundus imaging apparatus includes an illumination apparatus including a plurality of light sources and an illumination optical system. Examples of a suitable illumination apparatus include a configuration in which a plurality of light sources and an illumination optical system are disposed on a head-mounted device such as a head band.

Further, in the embodiment of the present invention, the fundus imaging apparatus may be provided together with another eye examination apparatus such as an eyesight examination apparatus, or may share a part of the configuration with another eye examination apparatus. This configuration is advantageous from a viewpoint of further spreading the fundus imaging apparatus according to the embodiment of the present invention.

Alternatively, in the embodiment of the present invention, the illumination apparatus and the imaging apparatus may be configured to be attachable to an information apparatus such as a smartphone that can realize information processing, as an accessory. In a case where the information apparatus includes a light and a camera, the light of the information apparatus may be used as the illumination apparatus according to the embodiment of the present invention within a range in which the effects of the embodiment of the present invention can be obtained. Further, the camera of the information apparatus may be used as the imaging apparatus according to the embodiment of the present invention within a range in which the effects of the embodiment of the present invention can be obtained.

In addition, in the embodiment of the present invention, the fundus imaging system may further include a simple diagnosis processing unit that performs processing of outputting simple diagnosis information according to the acquired image of the fundus. The processing can be realized by, for example, processing of determining an abnormality in the eyeball E based on a feature of the acquired image of the fundus and outputting information for recommending a medical examination at a medical institution or a possible disease name according to the determination result. The abnormality determination and the disease name determination can be realized by, for example, machine learning based on image data of the fundus including a specific abnormality. Further, the determination of the abnormality of the eyeball E can be realized by, for example, processing of referring to past information of the image of the fundus of a user and detecting a feature indicating that the fundus is in an abnormal state and a degree of the feature.

The functions of the control unit of the fundus imaging system according to the embodiment of the present invention can be realized by a program for causing a computer to function as the control unit, the program causing the computer to function as each control block of the control unit (in particular, each unit included in the control unit).

In this case, the control unit includes a computer including at least one control device (for example, a processor) and at least one storage device (for example, a memory) as hardware for executing the program. By executing the program by the control device and the storage device, each function described in each embodiment is realized.

The program may be recorded in not a transitory recording medium but one or a plurality of computer-readable recording mediums. The recording medium may be included in the device, or may not be included in the device. In the latter case, the program may be provided to the device via any wired or wireless transmission medium.

Further, some or all of the functions of the control blocks can be realized by a logic circuit. For example, an integrated circuit in which a logic circuit functioning as each control block is formed is also included in the scope of the present invention.

Further, the processing described in each embodiment may be executed by artificial intelligence (AI). In this case, the AI may operate in the control device, or may operate in another device (for example, an edge computer, a cloud server, or the like).

The present invention is not limited to the above-described embodiments, and various modifications may be made within a scope described in the claims. Also, an embodiment obtained by appropriately combining each technical means disclosed in different embodiments falls within a technical scope of the present invention.

SUMMARY

As is clear from the above description, according to an embodiment of the present invention, there is provided an optical system including: an illumination optical system (112) configured to irradiate a fundus of an eyeball (E) of a subject (H) with light from a light source (111); and an imaging optical system (122) configured to form an image of the fundus on an image sensor (121), in which an optical axis of the illumination optical system does not match an optical axis of the imaging optical system, or the illumination optical system does not have a specific optical axis. In addition, according to another embodiment of the present invention, there is provided a fundus imaging apparatus (10) including: an illumination apparatus (11) including a light source and the illumination optical system; and an imaging apparatus (12) including an image sensor and the imaging optical system. Further, according to still another embodiment of the present invention, there is provided a fundus imaging system (50) including the fundus imaging apparatus. Therefore, according to the embodiment of the present invention, it is possible to prevent occurrence of artifacts in fundus observation.

The illumination optical system may irradiate the fundus with the light from the light source via a trans-pars-plana region (27) of the eyeball. This configuration is more effective from a viewpoint of preventing the subject from feeling glare and from a viewpoint of more brightly illuminating the fundus.

Further, the illumination optical system may irradiate the fundus with the light from the light source via an iris-and-zonule-of-Zinn region (28) of the eyeball. This configuration is more effective from a viewpoint of preventing the subject from feeling glare and from a viewpoint of more brightly illuminating the fundus.

The illumination optical system may irradiate a surrounding tissue of the eyeball with the light from the light source via an eyelid of the subject. This configuration is more effective from a viewpoint of more reliably preventing the subject from feeling glare and from a viewpoint of more reliably preventing an occurrence of an artifact.

The illumination optical system may irradiate a surrounding tissue of the eyeball with the light from the light source via a skull of the subject. This configuration is more effective from a viewpoint of brightly illuminating the fundus.

The illumination optical system may irradiate the surrounding tissue of the eyeball with the light from the light source via a plurality of portions of the skull of the subject. This configuration is more effective from a viewpoint of brightly illuminating the fundus.

The illumination optical system may irradiate a surrounding tissue of the eyeball with the light from the light source via an ethmoidal bone of the subject. This configuration is more effective from a viewpoint of brightly illuminating the fundus from below or behind the eyeball.

The illumination optical system may irradiate the fundus with the light from the light source via an arc region (31) or an annular region (41) around an eye on a face of the subject. This configuration is more effective from a viewpoint of brightly illuminating the fundus.

A wavelength of the light from the light source may be 600 nm to 1600 nm. This configuration is more effective from a viewpoint of preventing a miosis reaction due to irradiation with the light from the light source and from a viewpoint of preventing attenuation of irradiation light due to absorption of the light into water in a living body.

The illumination apparatus may be disposed in contact with the subject. This configuration is more effective from a viewpoint of enhancing stability of conditions of the fundus imaging and from a viewpoint of simplifying the configuration of the fundus imaging apparatus.

The imaging apparatus may be disposed away from the subject. This configuration is more effective from a viewpoint of realizing non-contact fundus imaging with respect to the subject.

The fundus imaging system according to the embodiment of the present invention may further include a processing unit configured to perform processing of composing an image by adding a signal corresponding to light detected by the image sensor. This configuration is more effective from a viewpoint of acquiring many photon statistics.

The fundus imaging system according to the embodiment of the present invention may further include a processing unit configured to perform processing of imaging an internal structure of the subject from a signal corresponding to light detected by the image sensor. This configuration is more effective from a viewpoint of further enabling measurement by diffuse optical tomography.

What is claimed is:

1. An optical system comprising:
   an illumination optical system configured to irradiate a fundus of an eyeball of a subject with light from a light source; and
   an imaging optical system configured to form an image of the fundus on an image sensor, wherein
   an optical axis of the illumination optical system does not match an optical axis of the imaging optical system, the illumination optical system does not include an optical system of coaxial vertical illumination, or the illumination optical system does not have a specific optical axis, and
   an optical axis of emitted light in the illumination apparatus and an optical axis of received light in the imaging apparatus are independent from each other.

2. The optical system according to claim 1, wherein the illumination optical system irradiates the fundus with the light from the light source via a trans-pars-plana region of the eyeball.

3. The optical system according to claim 1, wherein the illumination optical system irradiates the fundus with the light from the light source via an iris-and-zonule-of-Zinn region of the eyeball.

4. An optical system comprising:
   an illumination optical system configured to irradiate a fundus of an eyeball of a subject with light from a light source; and
   an imaging optical system configured to form an image of the fundus on an image sensor, wherein
   an optical axis of the illumination optical system does not match an optical axis of the imaging optical system, the illumination optical system does not include an optical system of coaxial vertical illumination, or the illumination optical system does not have a specific optical axis,
   the illumination optical system irradiates a surrounding tissue of the eyeball with the light from the light source via an eyelid of the subject, and
   the fundus imaging system further includes an internal imaging processing unit that performs processing of imaging an internal structure of the subject from a signal corresponding to light detected by the image sensor.

5. An optical system comprising:
   an illumination optical system configured to irradiate a fundus of an eyeball of a subject with light from a light source; and
   an imaging optical system configured to form an image of the fundus on an image sensor, wherein
   an optical axis of the illumination optical system does not match an optical axis of the imaging optical system, the illumination optical system does not include an optical system of coaxial vertical illumination, or the illumination optical system does not have a specific optical axis,
   the illumination optical system irradiates a surrounding tissue of the eyeball with the light from the light source via a skull of the subject, and
   the fundus imaging system further includes an internal imaging processing unit that performs processing of imaging an internal structure of the subject from a signal corresponding to light detected by the image sensor.

6. The optical system according to claim 5, wherein the illumination optical system irradiates the surrounding tissue of the eyeball with the light from the light source via a plurality of portions of the skull of the subject.

7. The optical system according to claim 1, wherein the illumination optical system irradiates a surrounding tissue of the eyeball with the light from the light source via an ethmoidal bone of the subject.

8. The optical system according to claim 1, wherein the illumination optical system irradiates the fundus with the light from the light source via an arc region or an annular region around an eye on a face of the subject.

9. The optical system according to claim 1, wherein a wavelength of the light from the light source is 600 nm to 1600 nm.

10. A fundus imaging apparatus comprising:
    an illumination apparatus including a light source and the illumination optical system according to claim 1; and
    an imaging apparatus including an image sensor and the imaging optical system according to claim 1.

11. The fundus imaging apparatus according to claim 10, wherein the illumination apparatus is disposed in contact with the subject.

12. The fundus imaging apparatus according to claim 10, wherein the imaging apparatus is disposed away from the subject.

13. A fundus imaging system comprising the fundus imaging apparatus according to claim 10.

14. The fundus imaging system according to claim 13, further comprising: a processing unit configured to perform processing of composing an image by adding a signal corresponding to light detected by the image sensor.

15. The fundus imaging system according to claim 13, further comprising: a processing unit configured to perform processing of imaging an internal structure of the subject from a signal corresponding to light detected by the image sensor.

\* \* \* \* \*